United States Patent [19]

Moore

[11] Patent Number: 5,529,786
[45] Date of Patent: Jun. 25, 1996

[54] PROCESS AND PRODUCT FOR TREATMENT OF RHEUMATOID ARTHRITIS

[76] Inventor: Eugene R. Moore, 5600 Woodview Pass, Midland, Mich. 48642

[21] Appl. No.: 202,723

[22] Filed: Feb. 28, 1994

[51] Int. Cl.$^6$ ...................................................... A61K 9/20
[52] U.S. Cl. ........................ 424/464; 424/548; 424/571; 514/825
[58] Field of Search ..................................... 424/464, 548; 514/825

[56] References Cited

U.S. PATENT DOCUMENTS

| | | | |
|---|---|---|---|
| 4,444,752 | 4/1984 | Prudden | 424/95 |
| 4,601,896 | 7/1986 | Nugent | 424/36 |
| 4,704,273 | 11/1987 | McMichael | 424/85 |
| 5,075,112 | 12/1991 | Lane | 424/434 |
| 5,399,347 | 3/1995 | Trentham et al. | 424/184.1 |

FOREIGN PATENT DOCUMENTS 1041172  9/1966  United Kingdom .

*Primary Examiner*—Thurman K. Page
*Assistant Examiner*—James M. Spear
*Attorney, Agent, or Firm*—Merlin B. Davey

[57] ABSTRACT

This invention provides a therapeutic pill comprising animal tissue containing a therapeutic amount of Type II collagen and a method of preparing animal tissue containing Type II collagen for treatment of Rheumatoid Arthritis in humans.

5 Claims, No Drawings

PROCESS AND PRODUCT FOR TREATMENT OF RHEUMATOID ARTHRITIS

BACKGROUND OF THE INVENTION

Rheumatoid Arthritis is a painful and often crippling disease that initially results in swollen and imflammed joints, but often progresses to deformed or completely destroyed joints. This is a result of the body mistakenly attacking collagen, which is the major portion of cartilage tissue. Cartilage tissue serves the function of a lubricant in the joints, keeping bone from rubbing on bone. As the disease progresses and more of the cartilage is destroyed, bone does begin to wear on bone. This results in even more severe pain and ultimately destruction of the joint itself. As the disease progresses, the body sometimes attacks other collagen in the soft tissues of the body which can cause a variety of arthritis-related diseases.

In order to initiate the disease, it is apparent that an individual must have an inherent (perhaps genetic) susceptibility. Given this susceptibility, there is now strong evidence that the disease is initiated by exposure to the Epstein-Barr virus. The ability of the Epstein-Barr virus to initiate Rheumatoid Arthritis has been linked to a key amino acid sequence which is identical to a sequence found in human collagen. Thus, in generating antibodies to destroy the Epstein-Barr virus, the body generates antibodies that are also capable of attacking its own collagen. In a similar manner, arthritis has been initiated in rats by the intradermal injection of highly purified Type II collagen extracted from chicken cartilage or by the well known complete Freund Adjuvant.

It was also shown that rats could be prevented from getting arthritis or the effects greatly reduced from this injection of highly purified collagen. This was accomplished by feeding the same highly purified collagen to the rats for several days prior to the injection. It was also shown with rats that, once arthritis had been induced, the effects of the disease could be reduced by the oral administration of the same highly purified collagen. In a later study with humans having severe arthritis it has been shown that the oral administration of the highly purified collagen is similarly beneficial to humans in reducing the effects of the disease.

Oral administration of this highly purified collagen represents the very first treatment for arthritis that represented a cure rather than simply a slowing of the progression of the disease. This oral treatment is believed to cure arthritis by causing a desensitization to Type II collagen. After this desensitization, the body stops producing antibodies that destroy its own collagen (which is similar to Type II collagen). This process has been called "oral tolerization" which is a partially understood process which the body uses to stop a person's immune system from treating food as a hostile foreign body. If foreign proteins are introduced via the digestive system, the body automatically suppresses immune responses to these proteins rather than triggering an immune response. It is a treatment that has been used in the past to treat simple allergies such as poison ivy or pollen.

While this oral treatment with highly purified collagen represents a long sought and highly desired treatment for Rheumatoid Arthritis, the required highly purified Type II collagen is very difficult to prepare. Typically, it is extracted from the tiny xiphoid cartilages of 2.5 week old chicks. In a preparation of the past art, eighty animals are required to produce 19 g of cleaned xiphoid cartilage dissected free of surrounding tissue. It is typical of the past art to perform up to seven extractions on each batch of tissue to obtain collagen of the required purity.

The procedure of the past art is thus seen to have several serious deficiencies. An extremely large number of animals are required to obtain a small amount of the desired product. The purification procedure is very time consuming and complicated, requiring multiple extractions and precipitations. These multiple operations, in addition to being time consuming and difficult, offer many opportunities for microbiological contamination which would render the collagen unusable or even dangerous. Often an ultra filtration operation is required to remove contamination from the solubilized collagen prior to the final precipitation. These complications make the collagen unavailable to many sufferers of arthritis.

SUMMARY OF THE INVENTION

I have found that animal tissue containing undenatured Type II collagen can be successfully utilized in directly treating Rheumatoid Arthritis, thereby greatly increasing the supply and eliminating the complex purification process for the preparation of Type II collagen of the prior art.

I have further found that said animal tissue may be formed into pills suitable for human ingestion and containing a therapeutically effective amount of Type II collagen.

DETAILED DESCRIPTION

The animal tissue preferably employed in the practice of this invention is chicken cartilage as obtained from chicken less than about one year of age, although other animal tissue containing Type II collagen, such as bovine cartilage and the vitreous humor of eyes may be employed if desired. In preparing cartilage for oral administration to humans the cartilage is first dissected free of surrounding tissues and diced or comminuted. The diced cartilage is sterilized by means known in the art and formed into capsules containing therapeutic levels of Type II collagen, said levels being generally in the amount of from 0.1 to 0.5 mg of highly purified collagen. Since it takes about 1000 parts of cartilage to produce one part of the highly purified Type II collagen, it requires at least about 0.01 gram and preferably from about 0.1 to about 0.5 grams of animal tissue to provide a therapeutic dose. The effective use of more mature chickens is surprising in view of the prior art which teaches only the use of chicks of less than three weeks of age. The usefulness of the more mature chickens allows an almost 100 fold increase in the amount of harvestable collagen from a single animal. This, of course, makes the desired product more readily available in therapeutic quantities, and also greatly decreases the possibility of micro-contamination due to the reduced handling during separation from relatively few animals. It is also believed that cartilage containing Type II collagen may be obtained from a variety of animals, and that this cartilage will perform in a similar manner to the chicken cartilage.

The following examples further illustrate the present invention:

EXAMPLE 1.

A chicken purchased from the grocery store is assumed to have been raised under the strict governmental regulations which prevent sick or diseased chickens from entering the food supply. A never frozen chicken is purchased and washed well with a dilute detergent solution, then soaked for 20 minutes in a 400 ppm chlorine equivalent solution provided by addition of 8.01 g of a 5.25% solution of NaOCl solution to 1000 gm of water. Surface contamination is mostly removed or destroyed by this treatment. The knife to be used to remove the cartilage is sterilized by washing well, then exposing the blade briefly to a flame. Clean rubber gloves are used as the cartilage is carefully cut away from the chicken flesh, then clean paper towel is used to dry and wipe the cartilage clean of loosely adhering material. Soaking in 3% hydrogen peroxide solution for over 20 minutes further sterilizes the cartilage without denaturing the collagen. The cartilage can then be stored at home freezer temperatures in double Zip-Loc (Reg. TM) brand polyethylene bags. The cleanliness of the procedure is verified by placing some of the cartilage into sterility bottles (Fisher scientific, code #99100) at 35 C for 24 hours. The lack of turbidity indicates a lack of micro-organisms. Prior to ingestion, the cartilage tissue is removed from low temperature storage, carefully diced with a cleaned razor blade and separated into 0.1 g or 0.5 g portions.

EXAMPLE 2.

Safety is tested by ingestion of 0.5 g of the diced cartilage daily by a healthy male for one week during which time no gastrointestinal abnormalities are noted.

EXAMPLE 3.

Effectiveness is judged from the effect of oral ingestion of the diced cartilage in breakfast juice by a mature female suffering from severe rheumatoid poly-arthritis. Ingestion is continued for a period of four months. The dose is 0.1 g/day for the first month and 0.5 g/day for the remaining three months. The dose is initially given each morning at least 20 minutes before breakfast, on an empty stomach. After a few days the dose time is varied randomly and the type of juice is varied, usually orange or cranberry. It is noted toward the end of the study that the patient is gradually able to reduce the intake of her normal arthritis medicine (Lodine) without ill effects. During this treatment time a general decrease in pain in all joints is noted. Particularly, the ankle and the knee joints are noted to be less swollen and painful. Black and blue marks in the ankle areas are seen to be significantly diminished. Higher energy levels are noted.

EXAMPLE 4.

In a manner similar to Example 3, bovine cartilage is employed with similar desirable results.

EXAMPLE 5.

Bovine vitreous humor (eye) tissue is used after being prepared by careful dissection, blending, and centrifuging to obtain a solid pellet which is employed with similar desired results.

EXAMPLE 6.

In a manner similar to Example 3, three similar studies are carried out on three additional subjects each with advanced Rheumatoid Arthritis, the difference being that:

a. In the first case the cartilage doses are first diced and individually placed in about 50 ml of 0.1 molar acetic acid (obtained by dilution 1 part of a 5 wt % acetic acid to 8.32 parts total solution in recently boiled water). After sufficient time for a near equilibrium extraction (about 30 days in this case) of soluble collagen into the acetic acid solution, the entire dose (including the undissolved cartilage) is mixed with orange juice and consumed by the subject. The extraction is shortened if the cartilage is diced more finely.

b. In the second case, cartilage doses are also first diced and placed in 0.1 molar acetic acid. After sufficient time for a near equilibrium extraction of soluble collagen into the acetic acid solution, the undissolved material and any microcontamination is removed by filtration through a filter (such as produced by the Millipore Co.) fine enough to sterilize by such filtration.

c. In the third case the same procedure as in (a) is followed except instead of acetic acid solution, orange juice (which is in itself acidic) is used.

In all three cases beneficial improvement in the patient's symptoms of arthritis, similar but improved over Example 3 above, are seen.

EXAMPLE 7.

The preparation is similar to Example 6(b) above except a sample of the collagen solution, after filtration, has sodium chloride added until the concentration is 7 wt %. The solution immediately becomes turbid. On setting overnight a fine precipitate settles to the bottom. This precipitate is believed to be the desired Type II collagen. This conclusion is supported by the effectiveness of Example 6(b) above.

There thus surprisingly appears to be no need to require the highly purified Type II collagen over raw, undenatured, native, chicken cartilage containing the Type II collagen. The chicken cartilage is surprisingly found capable of countering the effects of arthritis and no problem is seen associated with ingesting of Type II collagen in the presence of Type I collagen and other inactive ingredients of chicken cartilage.

EXAMPLE 8.

Cartilage is prepared as in Example 1, except after being diced it is sterilized by two techniques to enable its shelf life to be extended without low temperature storage:

a. The diced cartilage is soaked in a 3% solution of hydrogen peroxide for about 20 hours, then surface moisture removed and dose size quantities stored in polyethylene bags an extended period of time at room temperature.

b. The diced cartilage is placed in polyethylene bags for sterilization by electron beam radiation. A wide variety of electron doses is used. The exact electron dose is not known but by variation of time under the electron beam of constant intensity, it is possible to understand relative doses of electrons. Samples with the basic dose are increased in increments of 1x, 2x, 3x to 10x and 100x. These samples are stored for an extended period of time at room temperature.

Samples from both a and b are judged for both sterility and effectiveness. Sterility is judged by obvious discoloration of the samples (unsterile if discolored) or by the use of sterility bottles as described in Example 1 for samples that were not discolored. Samples are judged for effectiveness using the same procedure as in Example 3 and 6. The results are summarized in Table I.

TABLE I

| Type of Sterilization | Dose | Sterility | Effectiveness |
| --- | --- | --- | --- |
| electron beam | 1x | no | not tested |
| electron beam | 2x | no | not tested |
| electron beam | 3x | ? | not tested |

TABLE I-continued

| Type of Sterilization | Dose | Sterility | Effectiveness |
| --- | --- | --- | --- |
| electron beam | 4x | ? | not tested |
| electron beam | 5x | yes | not tested |
| electron beam | 6x | yes | not tested |
| electron beam | 7x | yes | yes |
| electron beam | 8x | yes | yes |
| electron beam | 9x | yes | yes |
| electron beam | 10x | yes | yes |
| electron beam | 100x | yes | no |
| peroxide | 20 hrs. | yes | yes |

The results of Example 8 demonstrate that shelf life can be extended by two of the common techniques used for sterilization. It is anticipated that other techniques that will be apparent to those familiar with the sterilization art may also be used to extend shelf life if utilized within the proper range as shown by the example above. Too strong a treatment can render the cartilage ineffective, while too little will not completely enough sterilize. In each case, the best level of the sterilization treatment can be determined by simple experimentation as determined above or by use of laboratory animals as described in the art. In many cases, it will be desirable to encapsulate the cartilage before or after the sterilization treatment. While the above sterilization techniques will serve to extend the cartilage shelf life, refrigerated storage may be used to extend it even further. The encapsulation will serve to make the precise dose easier to distribute and administer to patients. This is a very important aspect of making the treatment available to the large number of people who suffer from Rheumatoid Arthritis.

EXAMPLE 9.

Cartilage is prepared as in Example 1, except after being diced it is encapsulated and then sterilized using the 7x electron beam treatment of Example 8.

a. The first technique for encapsulating involves use of preformed gelatin capsules that were previously prepared in such a way that they come apart to allow insertion of a dose or fraction of a dose into them. They have the shape of two cylinders, each with one rounded closed end and one rounded open end. The diameter of each cylinder is such that the outside diameter of one is the same or slightly smaller than the inside diameter of the other. When they are apart, the desired dose of cartilage is placed within the smaller diameter end and the other end slid over top to completely close the capsule with the cartilage inside. This is repeated until a number of capsules have been filled. The filled capsules are subjected to a 7x treatment of electron beam radiation as in Example 8, then tested for effectiveness in treatment of Rheumatoid Arthritis.

b. The second technique for encapsulation utilizes a gelatin solution to coat the diced particles of cartilage. The solution is prepared by dissolving 10 parts of a household gelatin (sold under the trade name of JELL-O by the General Foods Corporation of New York) into 8.7 parts of pure water. Dissolution takes place when heated to boiling in a microwave oven with periodical stirring. After dissolution is complete the solution is cooled slightly, then poured over single doses of diced cartilage on waxed paper. After thoroughly mixing (during cooling) until all the cartilage is coated, the material is formed into as small an area as possible and allowed to cool, which sets the shape. After sterilization as in 9(a), these capsules containing sterilized cartilage are found to be effective in treatment of Rheumatoid Arthritis. They are seen to have both the advantage of increased shelf life and that of convenience of use.

EXAMPLE 10.

Samples are prepared in accordance with sample a and b of Example 9 except instead of electron beam sterilization after being encapsulated, they are sterilized chemically prior to being encapsulated. Cartilage is sterilized by placement in a 3% solution of hydrogen perioxide for 10 hours, then surface moisture removed before encapsulation. Both samples are found to have the triple benefits of an increased shelf life, convenience of dosing and consuming, and effectiveness in treatment of Rheumatoid Arthritis.

EXAMPLE 11.

Samples are prepared and tested as in Example 10 except the 5.25% NaOCl solution of Example 1 is used for sterilization. Beneficial results similar to Example 10 are obtained.

EXAMPLE 12.

Samples are prepared and tested as in Example 10 except gaseous ethylene oxide is used for sterilization. Beneficial results similar to Example 10 are also obtained.

EXAMPLE 13.

Cartilage is prepared as in Example 1, except instead of being diced by hand, the cartilage is ground in the presence of liquid nitrogen. The resulting fine ground cartilage is then sterilized with hydrogen peroxide as in Example 1 and then made into a tablet shape by:

a. adding 15% of cornstarch paste as a binder and 15% calcium silicate as a disintegrator, to a dough mixer (AMF powder and dough mixer) and mixing until homogeneous;

b. the material is granulated while still wet;

c. the prepared wet granules are dried in a electric granule dryer at 60 degrees C., particles larger than 16 mesh were removed and ground to pass a 16 mesh screen;

d. the granules are mixed with 0.5% magnesium stearate as a lubricant and tablets are compressed on a tablet press machine using concave punches. Samples are found to have the same advantages as found in Example 12.

EXAMPLE 14.

In a manner similar to Example 9(a), the cartilage is prepared then, prior to encapsulation, dryed in an air oven at an average temperature of 110° F. until more than half its weight in water is lost. The samples are found to have the same advantages as Example 9(a) with the added advantages of improved shelf life, reduced volume, and better solids handling characteristics (which allows automatic capsule filling).

The advantages of encapsulating are well known in the art surrounding Pharmaceutical technology, Flavor and Odor technology, and the art of insecticides and herbicides. Techniques for forming tablets using a variety of binders, disintegrating agents and lubricants and other additives are described in detail by M. H. Rubinstein the psi book "Pharmaceutical Technology, Tabulating Technology, Volume 1, John Wiley and Sons, N.Y., 1987). Many of the well known techniques for encapsulating are explained in detail by Risch and Reineccius in the book, "Flavor Encapsulation", ACS Symposium Series 370, Am. Chem. Soc., Washington, D.C., 1988 and by M. H. Gutcho in the book "Microcapsules and Microencapsulation Techniques, Noyes Data Corp., N.J., 1976. As pointed out in these references, a wide variety of water soluble, food grade, polymeric materials may be used for encapsulating coatings. These may include carbohydrate and protein natural materials as well as synthetics such as polyvinyl alcohol, methylcellulose, and base soluble copolymers of maleic anhydride or acrylic acid. Protein based materials would include gelatin and gelatin derivatives, polypeptone, soy protein, and milk derived protein. Carbohydrate based agents would include hydrolized starches, lipophilic starches, and plant exudates.

Both batch drying and fluid bed drying may be used to combine the cartilage with the polymeric agents. While tray drying is slower, it offers the opportunity for agglomeration followed by grinding to preferred sizes. Fluid bed drying while coating with a spray allows nearly the originally particle sizes to be maintained.

The performance of the cartilage may be enhanced by the use of controlled release coatings. Typically, particles of cartilage would be coated with varying thicknesses of a slow dissolving coating. The thinner coatings would be dissolved instantly, while the thicker layers would require up to about 12 hours to dissolve.

The present human examples are based on information obtained from the studies with rats, and the 1000:1 published recovery ratio of cartilage to highly purified collagen. This translates to 0.1 or 0.5 gram cartilage per day. While there may be an optimum dose different from this, the administered dosage can vary widely without side effects as long as a minimal therapeutic dose is maintained. There are no adverse effects observed with doses ten fold or more higher than stated above. It is desirable ultimately to discontinue conventional immune system depression medication for arthritis in order to eliminate the undesired side effects associated with those immune system depression drugs. Other than side effects, however, there is no apparent need to discontinue the old medication before starting the cartilage treatment. The ability to continue the old medication while starting the new cartilage treatment provides the benefit of avoiding the frequent "arthritis shock" produced while switching medication.

Various modifications may be made in the present invention without departing from the spirit or scope thereof as will be readily apparent to those skilled in the art.

What is claimed is:

1. A therapeutic pill comprising animal tissue and containing a therapeutic amount of water-insoluble undenatured Type II collagen.

2. Therapeutic pill of claim 1 wherein said pill contains at least about 0.01 gram of animal tissue.

3. Therapeutic pill of claim 2 wherein the animal tissue is chicken cartilage.

4. Therapeutic pill of claim 2 wherein the animal tissue is bovine cartilage.

5. Therapeutic pill of claim 2 wherein the animal tissue is bovine vitreous humor.

* * * * *